United States Patent [19]

Marwil et al.

[11] 4,130,484

[45] Dec. 19, 1978

[54] PURIFICATION PROCESS

[75] Inventors: Stanley J. Marwil; Ernest A. Zuech, both of Bartlesville, Okla.

[73] Assignee: Phillips Petroleum Company, Bartlesville, Okla.

[21] Appl. No.: 700,422

[22] Filed: Jun. 28, 1976

[51] Int. Cl.² .......................................... B01D 15/00
[52] U.S. Cl. ...................................... 210/41; 55/35; 55/70; 55/75; 568/920; 568/921; 568/917
[58] Field of Search ................. 55/29, 33, 35, 70, 75; 210/24, 41; 252/455 Z; 423/237, 239; 260/643 F, 643 G

[56] References Cited

U.S. PATENT DOCUMENTS

| | | | |
|---|---|---|---|
| 2,137,605 | 11/1938 | Derr | 55/33 |
| 2,882,243 | 4/1959 | Milton | 260/643 G |
| 3,472,912 | 10/1969 | Quisenberry | 260/683.65 |
| 3,483,137 | 12/1969 | Sensel | 55/75 |
| 3,723,308 | 3/1973 | Breck | 210/38 |
| 3,733,391 | 5/1973 | Hoffman | 423/118 |
| 3,808,773 | 5/1974 | Reyhing et al. | 55/75 |
| 3,840,583 | 10/1974 | Turk et al. | 260/465.8 R |
| 3,852,252 | 12/1974 | DeVault et al. | 260/85.1 |
| 3,896,173 | 7/1975 | Drake | 260/583 P |

OTHER PUBLICATIONS

"Linde Molecular Sieves, Adsorbent Data," Union Carbide Corporation Technical Bulletin.

Primary Examiner—Charles N. Hart
Assistant Examiner—Ivars Cintins

[57] ABSTRACT

A process for removing at least a substantial portion of at least one contaminant from a fluid containing said at least one contaminant and at least one dehydration sensitive compound without causing substantial dehydration of said dehydration sensitive compound, said at least one contaminant being selected from the group consisting of water and nitrogen compounds having the formula $XNH_2$ wherein X is selected from the group consisting of hydrogen and linear alkyl radicals having 1 to 22 carbon atoms; which comprises contacting said fluid with a suitable base treated molecular sieve having an effective pore diameter in the range of about 2 to about 6 Angstrom units.

18 Claims, 1 Drawing Figure

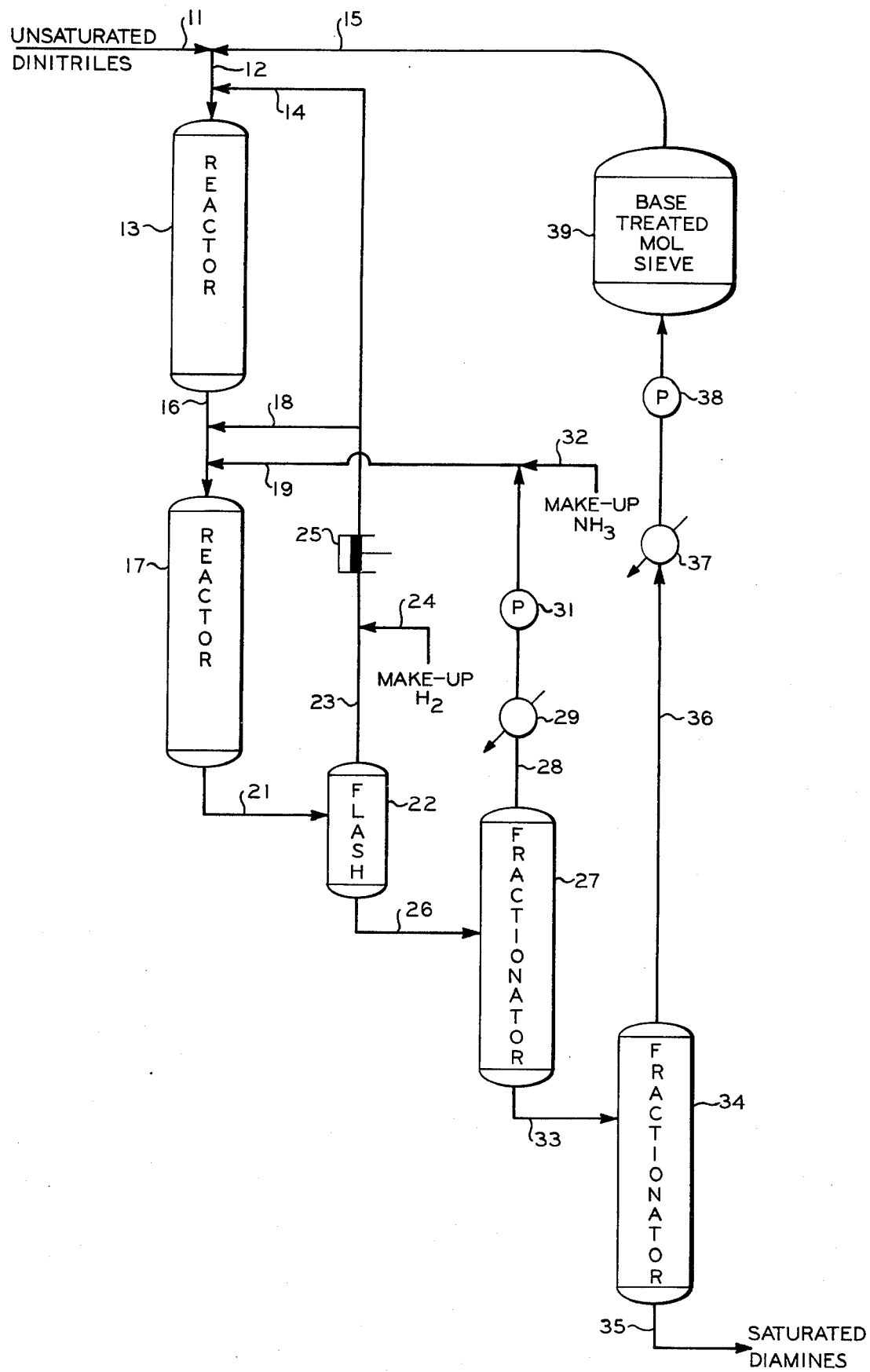

PURIFICATION PROCESS

This invention relates to the purification of a dehydration sensitive compound. In one aspect the invention relates to the use of a base treated molecular sieve to remove water, ammonia and/or primary amines from a dehydration sensitive compound, e.g. a secondary or tertiary alcohol. In another aspect the invention relates to a process for the hydrogenation of olefinically unsaturated dinitriles in two stages wherein ammonia is utilized in one stage and must be removed from the diluent before the diluent can be employed in the other stage.

The use of molecular sieves to remove water and/or ammonia from various feedstreams is known. However, if the feedstream contains a dehydration sensitive compound, the molecular sieve can cause the dehydration of a portion of the dehydration sensitive compound, thereby producing undesired contaminants as well as consuming part of the feedstream. Accordingly, it is an object of the present invention to provide a process for the removal of water, ammonia and/or primary amines from a feedstream containing at least one dehydration sensitive compound without causing significant dehydration of such compound. Another object of the invention is to provide a new and improved process for the hydrogenation of olefinically unsaturated dinitriles. A further object of the invention is to remove catalyst poisons from a stream before the introduction of the stream into a catalytic reaction. Other objects, aspects and advantages of the invention will be apparent from a study of the specification, the drawing, and the appended claims to the invention.

The foregoing objective can be accomplished in accordance with the present invention by contacting the feedstream with a suitable base treated molecular sieve having an effective pore diameter in the range of about 2 to about 6 Angstrom units. The untreated molecular sieve can be any suitable natural or synthetic crystalline zeolite material, but in general will be a synthetic Type A molecular sieve zeolite, with the commercially available 3A, 4A and 5A materials being preferred. The preparation of Type A zeolites is described for example in U.S. Pat. Nos. 2,882,243 and 3,078,636 of R. M. Milton. The base treatment of the molecular sieve material can be accomplished with any suitable base under any suitable conditions. In general, the hydroxides, carbonates and carboxylic acid salts of the alkali metals and the alkaline earth metals are considered to be suitable bases. Such carboxylic acid salts will normally be metal salts of mono- and di-carboxylic acids having from 1 to 18 carbon atoms, preferably from 1 to 10 carbon atoms, and more preferably from 1 to 4 carbon atoms. Specific examples of such bases include lithium carbonate, lithium hydroxide, lithium acetate, lithium formate, sodium carbonate, sodium hydroxide, sodium acetate, sodium propionate, potassium carbonate, potassium hydroxide, potassium acetate, potassium butyrate, rubidium carbonate, rubidium hydroxide, rubidium acetate, rubidium caprate, cesium carbonate, cesium hydroxide, cesium acetate, cesium stearate, calcium carbonate, calcium hydroxide, calcium acetate, calcium succinate, strontium carbonate, strontium hydroxide, strontium acetate, strontium adipate, barium carbonate, barium hydroxide, barium acetate, barium sebacate, barium octadecanedioate, and mixtures of any two or more thereof. The alkali metal hydroxides, carbonates and acetates are preferred, with sodium carbonate being particularly preferred because of ease of handling in glass or steel containers.

In general the molecular sieve material will be contacted with an aqueous solution of the base at a suitable temperature and pressure, for example a temperature in the range of about 10° to about 200° C at a pressure in the range of 0 to 1000 psig (0.1 to 6.9 MPa). If desired, the molecular sieve material can be exposed to humid air to increase the moisture content of the molecular sieve material prior to contact with the aqueous solution of the base. The treatment of the molecular sieve material with the base is continued for a period of time sufficient to reduce the dehydration characteristic of the molecular sieve material to the desired extent. In general the base treatment will be in the range of 10 minutes to 60 hours, preferably will be in the range of 1 hour to 40 hours, and more preferably will be in the range of 2 hours to 30 hours. After the base treatment, the molecular sieve material can be rinsed one or more times to remove excess base and then dried. The thus treated molecular sieve material will generally be activated in a suitable manner, for example by being heated to a temperature in the range of 500° C to 1200° C for a period of time in the range of about 15 minutes to about 24 hours.

The base treated molecular sieve can be employed to purify any fluid containing a dehydration sensitive compound and at least one contaminant selected from the group consisting of water and nitrogen compounds having the formula $XNH_2$ wherein X is hydrogen or a linear alkyl radical having from 1 to 22 carbon atoms. Exemplary contaminants which can be removed from such fluid include water, ammonia, methyl amine, ethyl amine, n-butyl amine, n-hexyl amine, n-decyl amine, n-undecyl amine, n-octadecyl amine, n-eicosyl amine, n-docosyl amine, and mixtures of any two or more thereof. The dehydration sensitive compound can be any compound which would be at least partially dehydrated in the presence of the untreated molecular sieve material but which is not significantly dehydrated in the presence of the base treated molecular sieve. The invention is applicable to the purification of fluids containing at least one secondary alcohol having 3 to 20 carbon atoms and/or at least one tertiary alcohol having 4 to 20 carbon atoms. Examples of secondary alcohols include 2-propanol, 2-butanol, 2-hexanol, 4-decanol, 2-eicosanol, 5-methyl-2-decanol and 3-ethyl-2-pentanol. Examples of tertiary alcohols include 2-methyl-2-propanol, 2-methyl-2-butanol, 3-methyl-3-pentanol, 3-ethyl-3-hexanol, 2-ethyl-2-hexanol, 2,4-dimethyl-2-pentanol, 2,3-dimethyl-3-pentanol, 3-ethyl-3-pentanol, 3,7-dimethyl-3-octanol, 3-ethyl-3-decanol, 2,4,6-trimethyl-4-dodecanol, and 3,5,7-diethyl-5-tetradecanol. The unsubstituted tertiary alkanols having 4 to 12 carbon atoms can be advantageously purified in accordance with the present invention.

The passage of the fluid, containing at least one dehydration sensitive compound and at least one contaminant selected from the group consisting of water and nitrogen compounds having the hereinabove defined formula $XNH_2$, through the base treated molecular sieve can be accomplished under any suitable conditions. Generally the temperature will be in the range of about 10° to about 75° C, and preferably will be in the range of about 20° to about 50° C. Pressures in the range of about 0.1 to about 6.9 Mpa are considered to be satisfactory for general purposes, with values in the range of about 0.1 to about 0.7 MPa being presently preferred.

While any suitable contact time can be employed, in general the contact time will be in the range of about 1 minute to about 6 hours, and preferably will be in the range of about 10 to about 60 minutes. The base treated molecular sieve can be in a single body or in a plurality of bodies in parallel and/or in series, as desired.

The single drawing is a diagrammatic illustration of a process for the hydrogenation of olefinically unsaturated dinitriles embodying the present invention. A feedstream comprising branched-chain unsaturated aliphatic dinitriles is passed through conduits 11 and 12 into trickle bed reactor 13 along with hydrogen from conduit 14 and a diluent comprising at least one tertiary alkanol from conduit 15. The reactor 13 is operated under reaction conditions to at least substantially reduce all of the olefinic unsaturation without any significant reduction of the nitrile groups. The reaction effluent, comprising saturated dinitriles, diluent and hydrogen, is passed through conduit 16 into second stage reactor 17 along with additional hydrogen from conduit 18 and ammonia from conduit 19.

The branched-chain unsaturated aliphatic dinitriles which are considered to be advantageously and efficiently hydrogenated in accordance with the process of this invention are the unsaturated dinitriles of the formula

wherein each R is independently selected from the group consisting of an alkylene radical and an alkylidene radical, and R' is an alkyl radical. Each R will generally have from 1 to 15 carbon atoms, preferably from 1 to 6, and more preferably from 1 to 3 carbon atoms. R' will generally have from 1 to 15 carbon atoms, preferably from 1 to 6 carbon atoms, and more preferably from 1 to 3 carbon atoms. In general, the unsaturated dinitrile reactant of formula (I) will contain from 7 to 30 carbon atoms, preferably from 8 to 16 carbon atoms, and more preferably from 9 to 12 carbon atoms.

Representative of unsaturated reactant species of formula (I) include such compounds as 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-8-dodecenedinitrile, 2,4,7,9,11,13,15-heptaethyl-6-hexadecenedinitrile, and mixtures of any two or more thereof.

If desired, other olefinically unsaturated dinitrile reactants can be present and effectively hydrogenated during the hydrogenation of the unsaturated dinitriles of formula (I). Thus, in addition to the unsaturated dinitrile reactants for formula (I), the dinitrile feedstock can contain one or more unsaturated dinitrile reactants of the formula

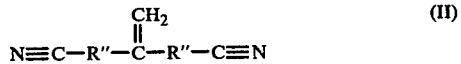

wherein each R" is independently selected from the group consisting of an alkylene radical and an alkylidene radical. In general, each R" will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures of any two or more thereof.

Unsaturated dinitriles having a structure other than that of formulas (I) and (II) can be present during the hydrogenation reaction, if desired. Similarly, other compounds which may be found in the feed source of the dinitriles of formulas (I) and (II) can be presentso long as such additional compounds do not significantly adversely affect the hydrogenation of the dinitriles of formulas (I) and (II). Where other dinitriles are present in the feedstock, the dinitriles of formula (I) will generally constitute at least 0.1 weight percent of the total dinitriles. The significant advantages of the process increase with increasing concentrations of the dinitriles of formula (I) in the feedstock. Thus, the process is even more advantageous for concentrations of the dinitriles of formula (I) in the feedstock of at least 5 weight percent. The process is considered to be particularly advantageous for dinitrile feedstocks having a concentration of the dinitriles of formula (I) of at least 10 weight percent.

A presently preferred branched-chain olefinically unsaturated aliphatic dinitrile feedstock for employment in the practice of this process is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to about 1:10.

Reactor 13 contains a suitable catalyst for the hydrogenation of the olefinic unsaturation, generally without significant reduction of the nitrile radical. Suitable catalysts include elemental platinum, elemental palladium and compounds of palladium and/or platinum which are reducible by hydrogen under the reaction conditions in reactor 13 to the finely divided elemental metal. Suitable reducible compounds include platinum oxide, platinum chloride, platinum nitrate, platinum sulfate, platinum oxalate, platinum acetate, platinum carbamate, platinum propionate, platinum tartrate, platinum hydroxide, palladium oxide, palladium chloride, palladium nitrate, palladium sulfate, palladium oxalate, palladium acetate, palladium carbamate, palladium propionate, palladium tartrate, palladium hydroxide, and the like, and mixtures of any two or more thereof.

Reactor 17 contains a suitable catalyst for the hydrogenation of the nitrile groups. Suitable catalysts include elemental cobalt, elemental nickel, elemental ruthenium, elemental rhodium, and compounds of one or more of these metals which are reducible by hydrogen under the reaction conditions in reactor 17 to the finely divided elemental metal, and mixtures of any two or more thereof. Suitable reducible compounds include the oxides, halides, nitrates, sulfates, oxalates, acetates, carbamates, propionates, tartrates, hydroxides and the like. Specific examples of suitable catalysts include Raney cobalt, elemental cobalt, cobalt oxide, cobalt chloride, cobalt acetate, cobalt hydroxide, elemental nickel, Raney nickel, nickel oxide, nickel bromide, nickel sulfate, nickel oxalate, nickel propionate, elemental ruthenium, ruthenium oxide, ruthenium nitrate, ruthenium carbamate, ruthenium hydroxide, elemental rhodium, rhodium oxide, rhodium chloride, rhodium nitrate, rhodium tartrate, rhodium hydroxide, and the like, and mixtures of any two or more thereof.

The weight ratio of catalyst to unsaturated dinitrile in reactor 13 can be varied as desired. Similarly the weight ratio of catalyst to saturated dinitrile in reactor 17 can be varied. In general, in each reactor the weight ratio of catalyst, calculated as elemental catalytic metal, to feed to be hydrogenated will be within a range of about 0.001:100 to about 30:100, preferably in the range of about 0.01:100 to about 5:100, and more preferably in the range of about 0.1:100 to about 0.6:100.

In the practice of this process, it is often desirable to employ catalytic amounts of the elemental metal, reducible compounds of the metal catalysts, or mixtures thereof supported by a solid catalyst carrier which does not deleteriously affect the catalytic hydrogenation process. Such supports include, for example, carbon, kieselguhr, silica, alumina, silica-alumina, calcium carbonate, barium carbonate, asbestos, pumice, clays, and the like, and mixtures thereof. The elemental metal or reducible compound catalyst components can be added to the catalyst support by any of the methods well known in the art. For example, the supported catalysts can be prepared by dry mixing the components or by impregnating the support with a solution or dispersion of the metal catalyst in elemental form or in the form of reducible compounds thereof. The supported catalyst can be pretreated with hydrogen to reduce the compounds, or such reduction can be achieved in the hydrogenation reactor. When a support is employed, the total elemental metal will generally be in the range of about 0.5 to about 50 weight percent, preferably in the range of about 1 to about 10 weight percent, based on the weight of the total catalyst composition. A presently preferred catalyst for first stage reactor 13 is palladium on carbon with the palladium content being about 5 weight percent of the total catalyst for reactor 13. A presently preferred catalyst for second stage reactor 17 is ruthenium on alumina, the ruthenium metal content being about 5 percent by weight, based on the weight of the total catalyst for reactor 17. These presently preferred catalysts, as well as other suitable catalysts such as 5 weight percent ruthenium on charcoal, are available commercially.

Any catalytic hydrogenation temperature can be employed which provides the desired degree of catalytic efficiency in the hydrogenation of the branched-chain unsaturated aliphatic dinitrile containing feedstock. The hydrogenation temperatures in the first stage will generally be within the range of about 30° C to about 200° C, and preferably will be within the range of about 70° C to about 150° C. The hydrogenation temperature in the second stage will generally be within the range of about 100° C to about 250° C, and preferably will be within the range of about 125° C to about 200° C.

The catalytic hydrogenation of the difficultly reducible carbon to carbon double bond illustrated in formula (I) can be carried out in the first stage at any suitable hydrogenation pressure. The catalytic hydrogenation of branched-chain saturated aliphatic dinitriles can be carried out in the second stage at any hydrogen pressure wherein the nitrile groups are reduced in the presence of ammonia, hydrogen and a suitable diluent. Generally, suitable hydrogen pressures for both stages are within the range of from about 500 to about 5000 psig (3.45 to 34.5 MPa), but lower or even higher hydrogen pressures can be employed. Preferably, due to economic considerations, hydrogen pressures within the range of about 1000 to about 3000 psig (6.9 to 20.7 MPa) are employed. It may be desirable to employ higher hydrogen pressures at lower reaction temperatures to achieve the desired degree of hydrogenation within a reasonable amount of time.

Any time interval suited for the desired catalytic hydrogenation in each stage can be employed in the practice of this process. However, time intervals economically attractive to the process are generally within the range of about 15 minutes to about 5 hours for the first stage of a batch hydrogenation process, and generally within the range of about 15 minutes to about 5 hours for the second stage of the batch process. A total reaction time in the range of about 1 to about 6 hours is presently preferred in order to insure substantially complete hydrogenation of any unsaturated olefinic bonds in the feedstock as well as complete hydrogenation of the nitrile groups to primary amino groups. The catalytic hydrogenation of unsaturated dinitriles in accordance with the process can be carried out as a continuous process at any suitable liquid hourly space velocity (LHSV). However, the liquid hourly space velocity rates will generally be within the range of about 0.1 to about 10, more preferably from about 0.5 to about 2 volumes of unsaturated dinitrile reactant plus diluent per volume of catalyst (including the volume of any catalyst support if any is present).

The diluent can be any suitable diluent, but the unsubstituted alkanols having from 1 to 12 carbon atoms per molecule, saturated hydrocarbons having from 4 to 12 carbon atoms per molecule and unsubstituted acyclic and unsubstituted cyclic ethers having 4 to 12 carbon atoms per molecule are preferred. The term "unsubstituted" indicates that there are no substituents other than hydrocarbyl radicals. Examples of alkanol diluents include methanol, ethanol, 2-propanol, 2-methyl-2-propanol, 2-methyl-2-butanol, 2-ethyl-2-hexanol, 2-butanol, 1-hexanol, 1-octanol, 2-decanol, 1-dodecanol, and the like, and mixtures of any two or more thereof. Examples of saturated hydrocarbons, i.e. alkanes and cycloalkanes, include butane, pentane, hexane, decane, dodecane, cyclobutane, cyclopentane, cyclohexane, cyclodecane, cyclododecane, 2-methylbutane, methyl-cyclopentane, 2,2,4-trimethylpentane, and mixtures of any two or more thereof. Examples of ethers include 1,3-dioxane, 1,4-dioxane, tetrahydrofuran, 4,4-dimethyl-1,3-dioxane, and mixtures of any two or more thereof. To facilitate handling of the reaction mixtures, the weight ratio of unsaturated dinitrile reactants to diluent charged to the reaction zone 13 is generally within the range of about 0.001:100 to about 15:100, and is preferably in the range of about 0.1:100 to about 12:100.

A secondary amine formation suppressant, e.g. ammonia, is employed in the second stage of the process as a means of suppressing undesirable side reactions such as the formation of secondary and tertiary amines. Any amount of the secondary amine formation suppressant can be employed which is effective in deterring or reducing undesirable side reactions. In general, the mole ratio of the secondary amine formation suppressant to cyano group (there being two cyano groups in each saturated dinitrile) will be in the range of about 1:1 to about 25:1, and preferably will be in the range of about 7:1 to about 15:1.

The effluent from reactor 17 is passed through conduit 21 to a flash tank 22* for the recovery of the hydrogen. The hydrogen is withdrawn from flash tank 22 by way of conduit 23 combined with make-up hydrogen from conduit 24 compressed by compressor 25 and passed through conduits 14 and 12 to reactor 13 The liquid is withdrawn from flash tank 22 and passed by way of conduit 26 into an intermediate portion of fractionator 27 for the removal of ammonia. The vaporous ammonia is withdrawn from an upper portion of fractionator 27 by way of conduit 28, condensed in heat exchanger 29, and passed by way of pump 31 and conduit 19, along with make-up ammonia from conduit 32, into second reactor 17. The liquid effluent from the lower portion of fractionator 27, which comprises diluent, saturated diamine products and small amounts of ammonia, is passed through conduit 33 into an intermediate portion of fractionator 34. A bottoms stream comprising saturated diamines is withdrawn from a lower portion of fractionator 34 by way of conduit 35. A vaporous overhead stream comprising diluent and a small amount of ammonia, e.g. about 500 ppm ammonia, is withdrawn from an upper portion of fractionator 34 and passed by way of conduit 36, containing condenser 37 and pump 38, into contact with a base treated molecular sieve in vessel 39. The diluent which is withdrawn from vessel 39 after contact with the base treated mole sieve contains a substantially reduced amount of ammonia, e.g. less than 1 ppm ammonia, and is passed through conduits 15 and 12 into reactor 13.

The following examples are presented in further illustration of the invention and should not be construed in undue limitation thereof.

EXAMPLE I

Approximately 400 ml (318.7g) of dry 5A mole sieve (0.32 mm extrudate) was treated overnight with wet air. The resultant material (372.6 g) was charged to a special glass tube (45 mm diameter) reactor equipped with an electrical heater. A solution of 200 g of anhydrous sodium carbonate in 4 lt of deionized water was prepared and the above sieve wet with this solution. The reactor was heated to 95°–97° C and the solution pumped through the bed upflow at approximately 140 ml per hour for 24 hours. After cooling, the material was washed 6 times with 350 ml of deionized water each time and then air dried on the filter overnight. After treating with Na$_2$CO$_3$, the 5A molecular sieves were activated for 8 hours at 600° F (315.5° C).

EXAMPLE II

A 50 ml buret was filled with 5A molecular sieve, which had not been base treated, but had been pre-wetted with tert-butyl alcohol and then tert-butyl alcohol contaminated with about 300 ppm ammonia was passed through the column at a rate of 100 ml/hr at room temperature of about 25° C and atmospheric pressure. Gas liquid chromatography analysis were made at hourly intervals. A total of 1000 ml of tert-butyl alcohol was passed through the column. No ammonia was detected in the effluent but 10–20 ppm isobutylene was formed by dehydration of the alcohol during the passage through the column.

A similar test was made using sodium carbonate treated 5A mole sieve prepared in Example I. Again, no ammonia ws detected and the isobutylene was of the effluent was less than 1 ppm. The tests showed that Na$_2$CO$_3$ modified 5A mole sieve was as effective in the removal of HN$_3$ as the untreated mole sieve and, in addition, that the formation of the undesirable isobutylene was almost completely suppressed.

EXAMPLE III

In order to test the life of the Na$_2$CO$_3$ treated 5A mole sieve, a larger sample of tert-butyl alcohol containing 500 ppm ammonia was prepared. The 50 ml buret was filled with Na$_2$CO$_3$ treated 5A mole sieve freshly prepared in accordance with Example I and the sample of NH$_3$ contaminated tert-butyl alcohol was passed through the column at a rate of approximately 100 ml/hr at room temperature of about 25° C and atmospheric pressure. The column was operated for 50 hours and 40 minutes and 4280 ml of effluent was collected. Intermittent NH$_3$ analysis showed less than 1 ppm NH$_3$ remaining in the effluent even after 50 hrs of column operation.

Reasonable variations and modifications are possible within the scope of the foregoing disclosure, the drawing and the appended claims to the invention.

That which is claimed is:

1. In a process for removing at least a substantial portion of at least one contaminant from a fluid containing said at least one contaminant and at least one dehydration sensitive compound, said at least one contaminant being selected from the group consisting of water and nitrogen compounds having the formula XNH$_2$ wherein X is selected from the group consisting of hydrogen and linear alkyl radicals having 1 to 22 carbon atoms wherein said fluid is contacted with a molecular sieve having an effective pore diameter in the range of about 2 to about 6 Angstrom units, thereby causing substantial dehydration of said dehydration sensitive compound; the improvement comprising treating said molecular sieve with at least one base selected from the group consisting of alkali metal hydroxides, alkali metal carbonates, alkaline earth hydroxides and alkaline earth carbonates and utilizing the thus treated molecular sieve to contact said fluid to thereby at least substantially reduce the dehydration of said dehydration sensitive compound.

2. A process in accordance with claim 1 wherein said at least one dehydration sensitive compound is selected from the group consisting of secondary alcohols and tertiary alcohols.

3. A process in accordance with claim 2 wherein said X is hydrogen.

4. A process in accordance with claim 2 wherein said at least one contaminant comprises ammonia.

5. A process in accordance with claim 4 wherein said at least one dehydration sensitive compound comprises at least one tertiary alkanol.

6. A process in accordance with claim 4 wherein said at least one dehydration sensitive compound comprises t-butanol.

7. A process in accordance with claim 6 wherein said base is a carbonate.

8. A process in accordance with claim 6 wherein said base comprises sodium carbonate.

9. A process in accordance with claim 2 wherein said at least one contaminant comprises water and at least one of said nitrogen compounds.

10. A process in accordance with claim 1 wherein said fluid contains water and at least one of said nitrogen compounds.

11. A process in accordance with claim 1 wherein said at least one contaminant comprises water and ammonia.

12. A process in accordance with claim 1 wherein said at least one contaminant comprises at least one of said nitrogen compounds.

13. A process in accordance with claim 1 wherein said at least one contaminant comprises ammonia.

14. A process in accordance with claim 1 wherein said contaminant comprises water.

15. A process in accordance with claim 1 wherein said molecular sieve is a 5A mole sieve.

16. A process in accordance with claim 15 wherein said at least one base comprises sodium carbonate.

17. A process in accordance with claim 16 wherein said at least one dehydratiion sensitive compound comprises at least one tertiary alkanol.

18. A process in accordance with claim 16 wherein said fluid comprises t-butanol and ammonia.

* * * * *